United States Patent [19]

Granath et al.

[11] Patent Number: 5,013,522

[45] Date of Patent: May 7, 1991

[54] METHOD FOR ANALYSIS OF PARTICULATE COMPOUNDS

[75] Inventors: Göran Granath, Göteborg; Gunnar Wikmark, Upsala, both of Sweden

[73] Assignee: ABB Atom AB, Västerås, Sweden

[21] Appl. No.: 427,483

[22] Filed: Oct. 27, 1989

[30] Foreign Application Priority Data

Oct. 27, 1988 [SE] Sweden .................. 8803840

[51] Int. Cl.⁵ .......................................... G21C 19/42
[52] U.S. Cl. ................................. 376/310; 376/305;
376/313; 436/43; 436/178
[58] Field of Search ............... 376/245, 305, 310, 313;
210/659, 198.2; 436/161, 43, 52, 177, 178, 181

[56] References Cited

U.S. PATENT DOCUMENTS

| | | | |
|---|---|---|---|
| 4,221,680 | 9/1980 | Hardwick et al. | 252/301.1 |
| 4,554,132 | 11/1985 | Collins | 436/43 |
| 4,608,153 | 8/1986 | Hudson et al. | 208/121 |
| 4,699,718 | 10/1987 | Jones et al. | 210/659 |
| 4,753,889 | 6/1988 | Collins | 436/20 |
| 4,801,551 | 1/1989 | Byers et al. | 436/133 |

Primary Examiner—Brooks H. Hunt
Assistant Examiner—Meena Chelliah
Attorney, Agent, or Firm—Watson, Cole, Grindle & Watson

[57] ABSTRACT

For determining the content and the chemical composition of particulate compounds in a liquid flow (15), the particulate compounds are collected on a filter (20) in a container (19) of a material which is permeable to microwaves. When carrying out the determination, samples of a fixed size of the liquid in the flow are supplied batchwise to the container on one side of the filter via an openable and a closable connection (16, 17) between the liquid flow and the container. At the same time, liquid from each liquid sample supplied batchwise, which has passed through the filter, is discharged from the container via an openable and a closable outlet (30, 31) on the other side of the filter. After closing of the connection between the liquid flow and the container and of the outlet for the liquid having passed through the filter, the container with the particulate compounds collected on the filter is supplied with a fixed amount of the solvent for the particulate compounds and the particulate compounds are dissolved in the solvent while being heated in a microwave oven. The solution of the particulate compounds, thus obtained, in each liquid sample supplied batchwise is led via an openable and a closable connection (33, 34) to an analysis apparatus (35) in which the composition and the content of one or more of the particulate compounds are determined. All actions, such as opening and closing of valves, heating processes and times for different operations, are controlled by automatic control.

7 Claims, 1 Drawing Sheet

METHOD FOR ANALYSIS OF PARTICULATE COMPOUNDS

BACKGROUND AND SUMMARY OF THE INVENTION

Nuclear power plants and other heat-generating power plants such as coal, oil, and gas power plants, are normally equipped with a circulation system for water, in which steam which is generated in a reactor vessel or in a steam generator connected to the circulation system is passed to a steam turbine, from there to a condenser and condensate formed therein, after cleaning and preheating, is returned to the reactor vessel of the steam generator.

In operation of power plants of the above-mentioned kinds different corrosion products are formed in the circulation system, inter alia in the form of oxides containing one or more metals of the kinds included in construction materials in the circulation system such as, above all, iron and further, inter alia, nickel, cobalt, chromium, manganese, titanium, molybdenum, zinc and zirconium. The corrosion products occur both as ionic dissolved compounds and as particulate undissolved compounds. In those cases where a nuclear reactor vessel is part of the circulation system, the corrosion products will become radioactive. Besides being influenced by the temperature, the amount and the nature of the corrosion products are influenced especially by the pH value of the water and the concentration of hydrogen and oxygen dissolved in the water. The corrosion products are therefore indicators of important properties of the water. By continuously investigating the corrosion products, it can be determined whether changes in the corrosion environment have occurred which require action regarding the operation of the power plant to eliminate the cause of the changes, such as, inter alia, changes of the pH of the water and, if a nuclear reactor vessel is included in the circulation system, inter alia the degree of radioactive contamination in the circulation system and the degree of oxide growth of cladding material for the fuel and of box material. It is, of course, of decisive importance for the operation of a power plant of the above-mentioned kinds that the water in the circulation system is as clean as possible to counteract the occurrence of corrosive coatings and an ensuing deteriorated economy.

When it comes to determining the chemical composition and the content of ionic dissolved compounds in water in water circulation systems of the kind described, automatic sampling systems have been produced, with the aid of which the nature and content of ionic compounds can be continuously followed during operation of the power plant. For analysis of particulate compounds, no corresponding automatic technique has been available. It has been necessary to separate the particulate compound from samples taken of the water on filters and then to determine the compounds by conventional methods by measuring directly on the filter or by dissolving the compounds in a solvent in a separate operation and analyzing the solution thus obtained in another separate operation. For analysis of this solution, a great number of methods can be used. In those cases where the analysis sensitivity is too low, the contents in the solution can be increased by using for analyses a larger water sample and hence a longer filtering time (enrichment time). Determination methods for solid samples for direct measurement of the particulate compounds on the filter are not applicable to water in water circulation systems of the kind described because of insufficient sensitivity.

According to the present invention, particulate compounds can be determined automatically in a sampling system in a reliable and simple manner, which includes a filtering of samples from the water in water circulation systems of the above-described kind or of liquid flows of another kind as well as dissolution of the particulate compounds, collected on the filter, in a solvent and determination of the nature and content of one or more of the particulate compounds in the solution obtained. For the dissolution known solvents for the particulate particles in question are used, and for analysis of the solution known analysis methods are used.

The invention is applicable not only to the analysis of particulate compounds in water in water circulation systems in power plants of the kinds described in the introduction, but also to the determination of particulate compounds in water of another kind and in liquids of another kind, such as spirit solutions and solutions of organic solvents, to the extent that these contain particulate compounds.

The present invention relates to a method of determining the chemical composition and the content of one or several particulate compounds in a flow of a liquid, whereby samples of the liquid are taken out from the flow and particulate compounds in the sample taken are collected on a filter through which the liquid in the sample is caused to pass, whereafter the collected particulate compounds are dissolved in a solvent while forming a solution in which the chemical composition and the amount of one or more of the particulate compounds are determined, characterized in that the filter is arranged in a closable container of a material permeable to microwaves; that samples of a fixed size of the liquid in the flow are supplied batchwise to the container on one side of the filter via an openable and a closable connection between the liquid flow and the container; that liquid, having passed through the filter, from each liquid sample supplied batch-wise is discharged from the container via an openable and a closable outlet on the other side of the filter; that after closing of the connection between the liquid flow and the container and of the outlet for the liquid having passed through the filter, a fixed amount of the solvent for the particulate compounds is supplied via an openable and a closable inlet to the container with particulate compounds from each liquid sample, supplied batchwise, collected on the filter and with the liquid from the liquid sample, supplied batchwise, discharged from the container; that the collected particulate compounds from each liquid sample, supplied batchwise, are dissolved in the solvent while heating the contents of the container by a microwave field from a microwave oven in which the container is arranged; and that the solution of the particulate compounds, thus obtained, in each liquid sample supplied batchwise is discharged via an openable and a closable outlet to an analysis apparatus, in which the composition and the content of one or more of the particulate compounds are determined.

The filter consists of a material which is resistant to the liquid to be analyzed and to the used solvent. Among suitable materials may be mentioned polytetrafluoroethylene and other fluorinated hydrocarbon polymers, for example polychlorotrifluoroethylene, as well as other resistant resins; further, inter alia, porcelain filters and sintered resistant particulate materials, for example sintered glass filters. The hole size of the filter is chosen in view of the size of the particulate compounds in the liquid flow. In most cases a hole size within the interval 0.2 μm–1.0 μm is suitable.

The container of a material permeable to microwaves also consists of a material which is resistant to the liquid to be analyzed and to the used solvent. Among suitable materials may be mentioned polytetrafluoroethylene and other fluorinated hydrocarbon polymers, for example polychlorotrifluoroethylene and glass. The volume of the container may suitably amount to 5–50 ml.

The particulate compounds are collected on the filter for a certain period of time. The time is chosen, depending on the particle content, such that a suitable amount of particles are collected on the filter. This amount should be such that it is suitable for analysis of the solution of the dissolved particulate compounds.

The solvents which are used for dissolution of the particulate compounds collected on the filter are, of course, dependent on the nature of the particulate compounds. For dissolution of corrosion products in water in a water circulation system in a nuclear power plant, as well as in other power plants of the kind described above, mixtures of acids may be used, preferably oxidizing such mixtures, as well as formers of chelate complexes. Mixtures of acids can be used for decomposition of most types of corrosion products of the kind described, whereas chelate formers are more specific. The chelate solutions usually have an optimum pH for dissolution in the interval 2–8. As examples of useful mixtures of acids may be mentioned mixtures of at least two of the acids hydrochloric acid, nitric acid, and perchloric acid. As examples of useful formers of chelate complexes may be mentioned ethylenediaminotetra acetic acid, citric acid and thioglycolic acid (HS—CH$_2$—COOH). The latter is particularly effective in mixtures with hydrochloric acid.

The time for dissolving a sample of particulate compounds varies with the sample quantity, the sample composition, the sample structure, the degree of atomization, the temperature, and the strength, pH and composition of the mixture of acids or the chelate solution. By heating the sample by microwaves, the rate of dissolution may be greatly reduced, from the order of magnitude of hours without microwave heating to the order of magnitude of minutes with microwave heating. The increased rate is assumed to be due to an increased convection in the solution and to an absorption of energy directly and locally in the grains of the particulate material.

The analysis of the solution of the particulate compounds is performed with known methods, for example by ion chromatography or by atom absorption spectrometry.

The method according to the invention operates on line, i.e., the sampling equipment used is connected to the liquid flow in which the nature and content of the particulate compounds are to be analyzed. All measures, such as opening and closing of valves, heating processes and times for different operations, are controlled by automatic control, preferably by computer control, for example comprising the use of microprocessors. In this way, a series of results is obtained from each sample taken batchwise from the liquid flow, thus obtaining an automatic determination of the particualte compounds for the whole of the time during which the determination is carried out.

The invention will be explained in greater detail, by way of examples, with reference to the accompanying drawings.

DETAILED DESCRIPTION OF THE PREFERRED EMBODIMENT

Figure 1:
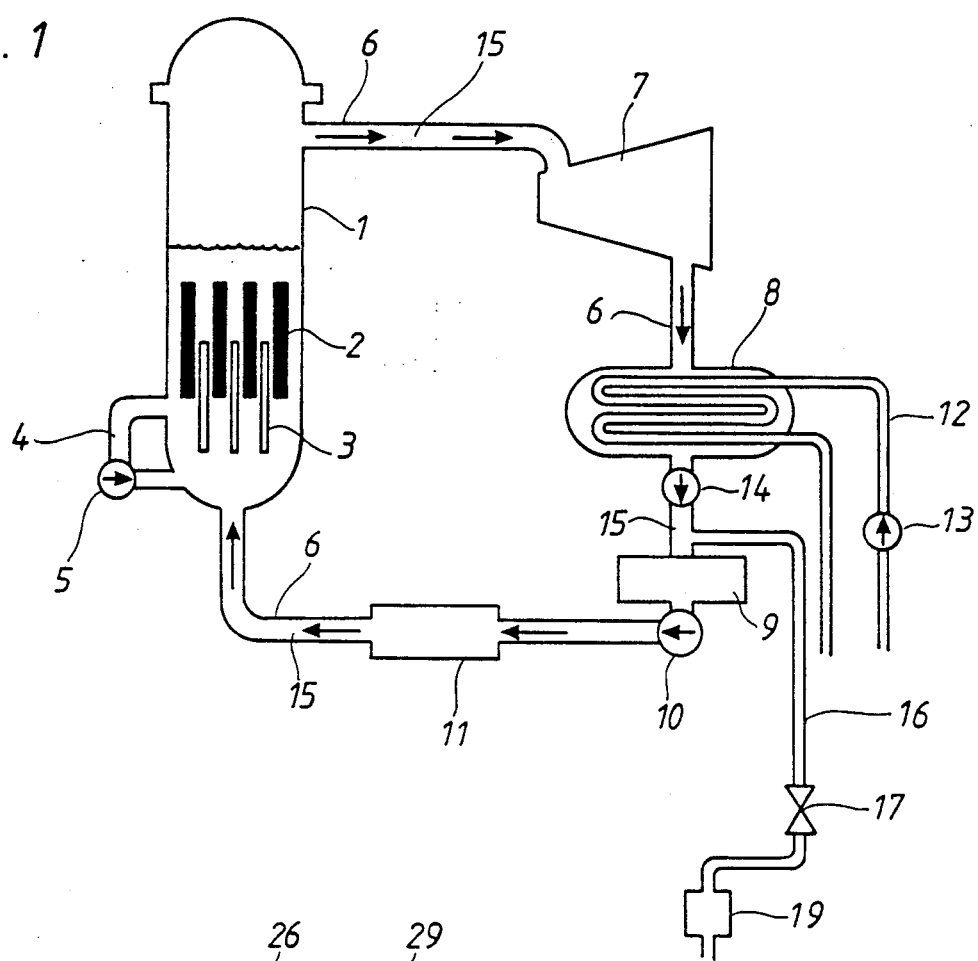
FIG. 1 schematically shows a boiling water reactor for a nuclear power plant with a water circulation system, and FIG. 2 schematically shows, on an enlarged scale, a sampling system for carrying out the method according to the present invention.

The boiling water reactor shown in FIG. 1 has a reactor vessel 1 with fuel elements 2, control rods 3 and main circulation systems 4, of which one is shown in the figure. Each main circulation system has a pump 5. The main circulation pumps ensure that the reactor core is sufficiently cooled. The reactor vessel is part of a water circulation system 6, which also comprises a steam turbine 7, a condenser 8, a condensate cleaning filter 9, pumps 10 and 14 and a preheater 11. The cladding material of the fuel elements consists of a zirconium alloy, for example Zircaloy-2. Steam generated in the reactor core gives its energy to the rotor of the turbine and is condensed, after passage of the turbine, in the condenser with a coolant circuit 12 comprising a pump 13. The condensate from the condenser 8 is transported by the condensate pump 14 through the condensate cleaning filter 9 and the condensate cleaned therein is fed, after preheating in preheater 11, into the reactor vessel by the feed pump 10. In the exemplified case the condensate cleaning filter comprises an ion-exchange filter with an ion-exchange compound in the form of a mixture of an anion-exchange compound (polystyrene with quaternary ammonium groups cross-linked with divinyl benzene) and a cation-exchange compound (sulphonated polystyrene cross-linked with divinyl benzene). According to the invention, samples of the water 15, the reactor water (in the illustrated case in the form of feed water), are taken batchwise from the circulation system 6 via the conduit 16 with the valve 17 and a sampling system, as shown in FIG. 2.

Figure 2:
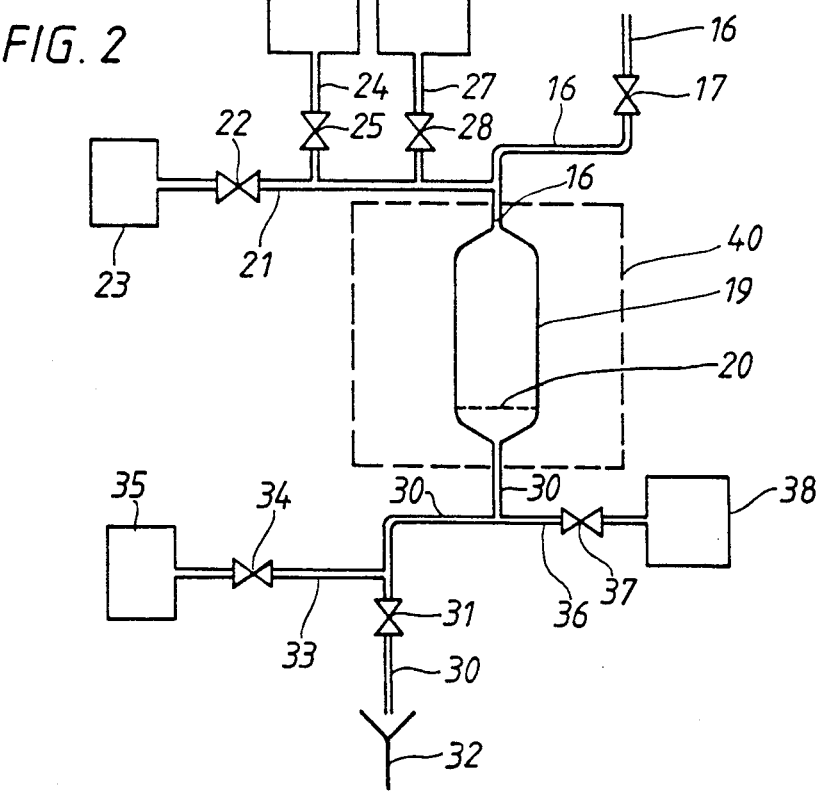

The sampling system exemplified in FIG. 2 includes a sealable container 19 of polytetrafluoroethylene with a volume of 25 ml. Only this part of the sampling system is shown in FIG. 1. The lower part of the container is provided with a filter 20 of polytetrafluoroethylene, the through-holes of which have a size of 0.45 μm. Via a conduit 21 with a valve 22 the container is connected to a tank 23 with a pressure gas in the form of nitrogen gas of a pressure of around 0.5 MPa, via another conduit 24 with a valve 25 it is connected to a tank 26 with solvent in the form of a mixture of 4 part by volume concentrated hydrochloric acid and 1 part by volume thioglycolic acid, via a conduit 27 with a valve 28 it is connected to a tank 29 with high purity water, via a conduit 30 with a valve 31 it is connected to a discharge 32, via a conduit 33 with a valve 34 it is connected to an apparatus 35 for analysis of the solution of particulate compounds, dissolved on the filter, in the reactor water by ion chromatography, and via a conduit 36 with a valve 37 the container is connected to an apparatus 38 for analysis of ionic dissolved compounds in the reactor water, also by ion chromatography. All the valves, i.e., valves 17, 22, 25, 28, 31, 34 and 37, are openable and closable. The container 19 is placed in a microwave oven 40, which is schematically illustrated by dashed lines in FIG. 2.

In the application of the method according to the invention in the exemplified case, a specified amount of the reactor water 15 is led via the conduit 16 to the container 19, through the filter 20 and via the conduit 30 to the discharge 32, particulate compounds present in the reactor water being collected on the filter. During this process the valves 17 and 31 are held open whereas the other valves are closed. The amount of reactor water or the time for its supply and passage through the container is adapted such that a quantity of particulate compounds, suitable for analysis, is collected on the filter.

When the specified amount of reactor water has traversed the container, the valve 17 is closed and the valve 22 is opened to empty the container of all possibly remaining liquid with a flow of nitrogen gas from the tank 23. After closing the valve 22 and the valve 31, the valve 25 is opened and a specified quantity of solvent is supplied to the container 19 from the tank 26 via the conduit 24, so that most of the volume of the container is filled with solvent. The remaining volume, consisting of nitrogen gas, functions as a pressure-equalizing gas volume. After the supply of this quantity of solvent, the valve 25 is closed. Then the container is heated with the microwave oven 40 for a definite period of time to a temperature which is sufficient for the particulate compounds collected on the filter to be dissolved for certain. After this operation, the valves 22 and 34 are opened, the container 19 with gas pressure being emptied of the solution of the particulate compounds present therein while the solution is being transported to the apparatus 35 for analysis by ion chromatography. After emptying the container, the valves 22 and 34 are closed. In the ion chromatograph 35 a chromatogram is taken up in a conventional manner, which shows the nature and the content of the elements included in the particulate compounds and hence the quantity of these particulate compounds in the batch of the reactor water taken out via the conduit 16. After closing of the valves 22 and 34, the container 19 is washed with water from the storage 29 by opening the valves 28 and 31. After closing of the valve 28 and opening of the valve 17, the whole process described above is repeated, which is thus started by supplying a new batch of the reactor water to the container 19 while keeping the valves 17 and 31 open for a specified time and keeping the other valves closed.

By repeatedly withdrawing batches of the reactor in the manner described, preferably with the same time intervals during operation of the reactor, it is possible continuously to follow the composition and content of the particulate compounds in the reactor water and then to determine whether changes of the reactor water have occurred which necessitate taking measures regarding the operation of the reactor to eliminate the cause of the changes.

Opening and closing of all valves in the illustrated device, as well as the microwave heating, are controlled by automatic control, preferably by computer control comprising microprocessors.

The exemplified device can also be used for analysis of ionic compounds in the reactor water. In such case the withdrawn sample of the reactor water, which has passed through the filter 20 in the container 19, is passed via the conduit 36 to the analysis apparatus 38 instead of via the conduit 30 to the discharge 32. During this process the valve 37 is kept open and the valve 31 is kept shut.

We claim:

1. A method of determining the chemical composition and content of particulate compounds in a flowing liquid using an analyzing apparatus for the particulate compounds and a sealable container positioned in a microwave oven, the sealable container being made of a material that is permeable to microwaves and containing a filter for the particulate compounds, said method comprising the steps of:
   (a) withdrawing a batch sample of fixed volume from said flowing liquid and passing said sample into said container,
   (b) causing said sample to pass through said filter in said container to deposit the particulate compounds in the sample on the filter and provide a permeate,
   (c) removing the permeate from the container,
   (d) supplying a fixed amount of solvent for the particulate compounds into the container to contact the particulate compounds on the filter,
   (e) passing microwaves into the container from the microwave oven to heat the solvent and particulate compounds therein and cause the particulate compounds to dissolve in the solvent, forming a solution, and
   (f) passing the solution to the analysis apparatus for analysis of the particulate compounds therein.

2. The method of claim 1, wherein during steps (b) and (c) a gas is passed through said container.

3. The method of claim 1, including after step (f) a step of passing cleaning water through said container.

4. The method of claim 1, wherein said solvent is a mixture of hydrochloric acid and thioglycolic acid.

5. The method of claim 1, wherein said filter is made of a fluorinated hydrocarbon polymer.

6. The method of claim 1, wherein said flowing water is the water in a recirculation system of a nuclear reactor.

7. The method of claim 1, including repeating steps (a)-(f) a plurality of times so as to obtain a series of determinations of chemical composition and content of particulate compounds in said flowing liquid over a period of time.

* * * * *